United States Patent [19]

Fleet et al.

[11] Patent Number: 5,100,797

[45] Date of Patent: Mar. 31, 1992

[54] FUCOSIDASE INHIBITORS

[75] Inventors: George W. J. Fleet; Sung K. Namgoong, both of Oxford, United Kingdom

[73] Assignee: Monsanto Company, St. Louis, Mo.

[21] Appl. No.: 371,943

[22] Filed: Jun. 27, 1989

[51] Int. Cl.$^5$ .............. C12N 9/24; C07H 5/06; C07D 211/40; A61K 31/73
[52] U.S. Cl. .............. 435/200; 536/1.1; 536/18.7; 536/55.3; 514/315; 546/184
[58] Field of Search .......... 536/1.1, 18.7, 55.3; 435/200; 514/315, 413, 23; 546/184, 242

[56] References Cited

U.S. PATENT DOCUMENTS

| | | | |
|---|---|---|---|
| 4,328,233 | 5/1982 | Böshagen et al. | 424/267 |
| 4,849,430 | 7/1989 | Fleet et al. | 514/315 |
| 4,861,892 | 8/1989 | Fleet | 546/219 |
| 4,992,460 | 2/1991 | Fleet | 514/413 |
| 4,996,329 | 2/1991 | Fleet et al. | 548/453 |
| 4,999,360 | 3/1991 | Fleet et al. | 514/315 |

OTHER PUBLICATIONS

Boeshagen et al; Chemical Abstracts 93:132381e (1980).
Boeshagen et al; Chemical Abstracts 95:187557p (1981).
Winchester et al; Biochem. J. 265:277-282 (1990).
Daher et al; Biochem. J. 258:613-615 (1989).
Kite et al., Tetrahedron Lett. 29, 6483-6486 (1988).
Liu et al., J. Org. Chem. 52, 4717 (1987).
Rhinehart et al., J. Pharmacol. Exptl. Therap. 241, 915-920 (1987).
Fleet et al., J. Chem. Soc. Perkin Trans. 1, 665-666 (1989).
Fleet et al., FEBS Lett. 237, 128-132 (1988).
Karpas et al., Proc. Natl. Acad. Sci. U.S.A. 85, 9929-9233 (1988).
Fleet et al., Tetrahedron 45, 319-326 (1989).
Fleet et al., Tetrahedron Cell. 29, 2871-2874 (1988).

*Primary Examiner*—Johnnie R. Brown
*Assistant Examiner*—Nancy S. Carson
*Attorney, Agent, or Firm*—Scott J. Meyer; James W. Williams, Jr.

[57] ABSTRACT

The synthesis of the novel fucosidase inhibitors, β-L-homofuconojirimycin and related 1-β-C-substituted deoxymannojirimycins, is disclosed.

6 Claims, 1 Drawing Sheet

FUCOSIDASE INHIBITORS

BACKGROUND OF THE INVENTION

This invention relates to novel fucosidase inhibitors. More particularly, the invention relates to the synthesis of β-L-homofuconojirimycin and related 1-β-C-substituted deoxymannojirimycins.

Both deoxynojirimycin (1) and α-homonojirimycin (2), the first example of a naturally occurring azapyranose analogue of a heptose recently isolated from *Omphalea diandra L.*, are potent inhibitors of α-glucosidase activity. See Kite et al., *Tetrahedron Lett.* 29, 6483-6486 (1988). Iminoheptitols such as (2) provide the opportunity for the synthesis of a class of stable aza-disaccharides such as (3) which may confer additional potency and/or specificity in comparison with the corresponding azapyranose analogues such as deoxynojirimycin; for example, the β-D-glucopyranosyl derivative (3) of α-homonojirimycin was first designed as a synthetic transition state inhibitor of α-glucosidases. See Liu, *J. Org. Chem.* 52, 4717 (1987). It is in clinical trials in relation to the treatment of diabetes mellitus. See Rhinehart et al., *J. Pharmacol. Exptl. Therapeut.* 241, 915-920 (1987).

1,5-Dideoxy-1,5-imino-L-fucitol, also referred to as deoxyfuconojirimycin (DFJ) (4), readily prepared from D-lyxonolactone [Fleet et al., *J. Chem. Soc. Perkin Trans.* 1, 665-666 (1989)], is a very powerful and highly specific inhibitor of a number of mammalian α-L-fucosidases. Some fucosidase inhibitors have potential as antiretroviral agents. See Fleet et al., *FEBS Lett.* 237, 128-132 (1988); Karpas et al., *Proc. Natl. Acad. Sci. USA* 85, 9229-9233 (1988); and copending applications Ser. No. 07/248,461, filed Sept. 23, 1988, now U.S. Pat. No. 4,349,430 and Ser. No. 7/249,144, filed Sept. 26, 1988, now U.S. Pat. No. 4,999,360.

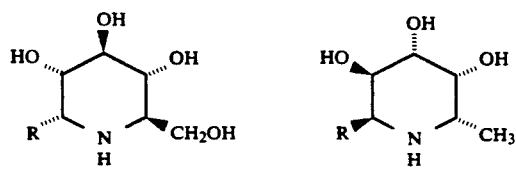

(1) R = H
(2) R = CH₂OH
(3) R = CH₂O-β-glucopyranosyl (4) R = H
(5) R = CH₂OH

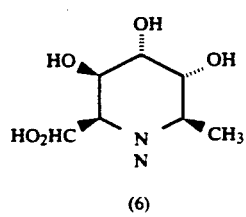

(6)

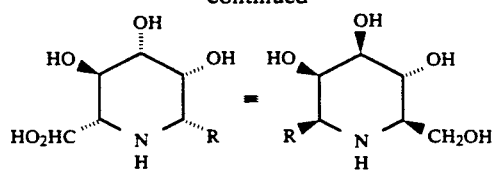

(7) R = Me β-L-homofuconojirimycin
(8) R = Et β-1-C-ethyl-deoxymannojirimycin
(9) R = Ph β-1-C-phenyl-deoxymannojirimycin
(10) R = H

BRIEF DESCRIPTION OF THE INVENTION

In accordance with the present invention, the novel fucosidase inhibitors β-L-homofuconojirimycin, also referred to as β-methyl deoxymannojirimycin, and related 1-β-C-substituted deoxymannojirimycins have been synthesized. The preferred 1-β-C-substituted deoxymannojirimycins are the β-methyl, β-ethyl and β-phenyl derivatives, although other novel β-alkyl derivatives having from one to about six carbon atoms in the alkyl group can be similarly prepared.

The novel fucosidase inhibitors of the invention have been synthesized in a series of steps from the 5-azido-6-O-tert-butyldimethylsilyl-5-deoxy-2,3-O-isopropylidene-D-mannono-1,4-lactone. The latter material is a known compound which was prepared from the commercially available L-gulonolactone as previously disclosed in copending application Ser. No. 07/249,153, filed Sept. 26, 1988, now U.S. Pat. No. 4,861,892, and published by Fleet et al., *Tetrahedron* 45, 319-326 (1989) and *Tetrahedron Lett* 29, 2871-2874 (1988).

All the novel compounds of the invention prepared herein are potent and specific competitive inhibitors of human liver α-L-fucosidase (see Table 1, below, and the Figure); thus the introduction to DFJ (4) of an anomeric hydroxyl group with the wrong configuration to give β-L-homofucononojirimycin (7) did not diminish the inhibition of α-L-fucosidase. When the methyl group in (7) was substituted for ethyl, it was found that β-ethyl DMJ (8) was still a very powerful fucosidase inhibitor. Even β-phenyl DMJ (9), with the methyl group substituted by a large aromatic group, is a more potent fucosidase inhibitor than is DMJ (10), where the methyl group is replaced by hydrogen. The 6-epi-α-L-homonojirimycin (6), with the correct anomeric hydroxyl group but with the wrong stereochemistry of the methyl group, is 500 times weaker an inhibitor than is (7) with the correct methyl chirality but the wrong anomeric configuration. It is noteworthy that only DMJ (10) showed any inhibition of mannosidase activity; none of the other compounds caused any significant inhibition of mannosidase activity. Since none of the alkylated deoxymannojirimycins are mannosidase inhibitors but all are fucosidase inhibitors, it is apparent that the ability of derivatives of DMJ (10) to inhibit mannosidases is highly sensitive to substituents at the C-1 position.

It is also shown herein that a suitably protected hydroxymethyl group can control the hydrogenation stereochemistry of the imine regardless of the other groups on the piperidine ring.

DETAILED DESCRIPTION OF THE INVENTION

Figure 1:
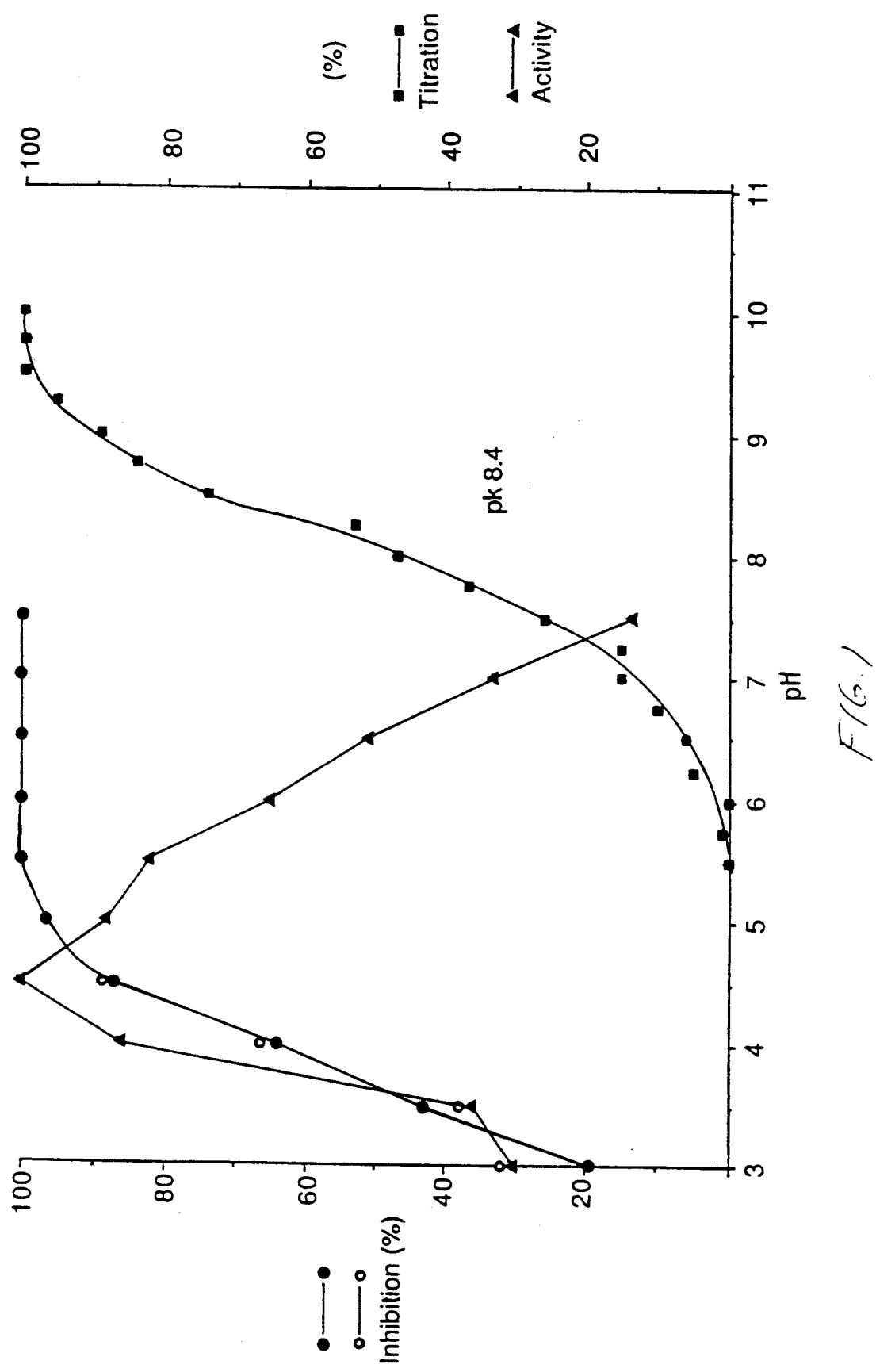

While the specification concludes with claims particularly pointing out and distinctly claiming the subject matter regarded as forming the present invention, it is believed that the invention will be better understood from the following detailed description of preferred embodiments of the invention taken in conjunction with the appended drawing, in which:

FIG. 1 is a graphical representation which shows the inhibition of human liver α-L-fucosidase by β-L-homofuconojirimycin (N-Me DFJ) and by a control compound, deoxyfuconojirimycin (DFJ). The activity of the enzyme was measured in the absence (▲) and presence of DFJ (●) and N-Me DFJ (o). Inhibition was measured as a percentage of uninhibited reaction. Titration curve by DFJ (■).

Short syntheses of β-L-homofuconojirimycin (7) and the other 1-β-C-substituted deoxymannojirimycins (8) and (9) began from the azidolactone (17). Thus addition of methyl lithium to (17) gave the adduct (18) in 72% yield which on hydrogenation in the presence of a catalyst of platinum(IV) oxide gave a single piperidine (21), m.p. 93°-94° C., $[\alpha]_D^{20}$ −47.3° (c, 1.06 in CHCl$_3$), in 86% yield. Both the silyl and isopropylidene protecting groups were removed from (21) to give β-L-homofuconojirimycin [β-1-C-methyl deoxymannojirimycin] (7), m.p. 97°-98° C., $[\alpha]_D^{20}$ −21.5° (c, 1.07 in H$_2$O), in 95% yield. Addition of vinyl magnesium bromide to azidolactone (17) gave the monoadduct (19) (90%) which on hydrogenation gave (22), m.p. 55°-56° C., $[\alpha]_D^{20}$ −37.7° (c, 1.26 in CHCl$_3$), in 80% yield. Subsequent acid hydrolysis of (22) gave β-1-C-ethyl deoxymannojirimycin (8), m.p. 54°-56° C., $[\alpha]_D^{20}$ −6.5° (c, 1.07 in H$_2$O), in 95% yield. Similarly, addition of phenyl magnesium bromide to (17) gave (20) (86% yield) which on hydrogenation gave (23), m.p. 86°-87° C., $[\alpha]_D^{20}$ 0.0° (c, 1.05 in CHCl$_3$), in 81% yield; hydrolytic removal of the protecting groups afforded β-1-C-phenyl deoxymannojirimycin (9), m.p. 77°-79° C., $[\alpha]_D^{20}$ +62.0° (c, 0.57 in H$_2$O), in 90% yield. For each of the protected heptitols the small value of the coupling constant between H-1 and H-2 (J$_{1,2}$2.5-2.6 Hz) in contrast to that between the trans-diaxial protons, H-4 and H-5 (J$_{4,5}$=10.0-10.1 Hz) indicates a cis relationship between H-1 and H-2; thus the hydrogenation of the C=N proceeds consistently and exclusively from the least hindered face.

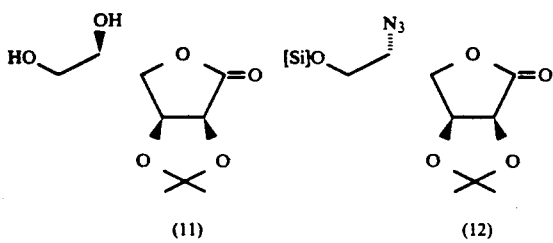

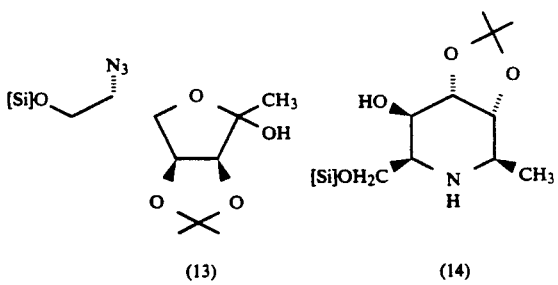

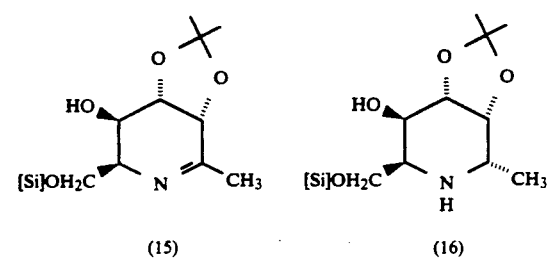

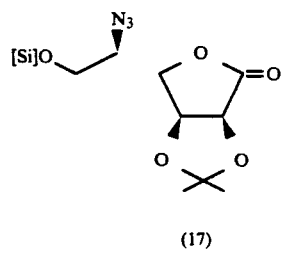

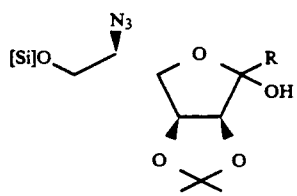

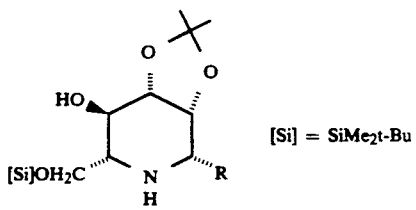

It will be appreciated that the novel fucosidase inhibitors of the invention can exist in the free base form as well as in biologically and pharmaceutically acceptable salt forms such as, e.g., the HCl, acetate, carbonate, sulfate, oxalate and the like.

The following examples will further illustrate the invention although the invention is not limited to these specific examples.

METHODS

M.p.s were recorded on a Kofler block. Infra red spectra were recorded on a Perkin-Elmer 297 spectrophotometer. Optical rotations were measured on a Perkin-Elmer 241 polarimeter; concentrations are given in g/100 ml. $^1$H NMR spectra were run at 200 MHz on a Varian Gemini spectrometer, or at 300 MHz on a Bruker WH 300 spectrometer or at 500 MHz on a Bruker AM 500 spectrometer; COSY spectra were routinely used in interpretation of the spectra. $^{13}$C NMR spectra were recorded on a Varian Gemini (50 MHz) or a Bruker AM 250 (62.9 MHz) or a Bruker AM 500 (125.0 MHz) spectrometer. For NMR spectra in D$_2$O, 1,4-dioxane ($\delta$ 67.7) was used as an internal standard. Mass spectra were recorded on VG Micromass ZAB 1F or MM 30F spectrometers. Microanalyses were performed by the microanalytical services of the Dyson Perrins Laboratory, Oxford, U.K. TLC was performed on aluminum pre-coated silica gel (Merck) plates, and compounds were visualized with a spray of 0.2% w/v concentrated sulphuric acid and 5% ammonium molybdate in 2N sulphuric acid. Flash chromatography was carried out using Merck Kieselgel 60, 230–400 mesh. Tetrahydrofuran was distilled from a solution dried with sodium in the presence of benzophenone under dry nitrogen. L-Gulonolactone was obtained from Sigma Chemical Company and was converted into 5-azido-6-O-tert-butyldimethylsilyl-5-deoxy-2,3-O-isopropylidene-D-mannono-1,4-lactone (5) as previously described in co-pending Application Ser. No. 249,153, filed Sept. 26, 1988, now allowed, and by Fleet et al., *Tetrahedron* 45, 319–326 (1989) and *Tetrahedron Lett.* 29, 2871–2874 (1988).

EXAMPLE 1

1-C-Methyl 5-Azido-6-O-tert-butyldimethylsilyl-2,3-O-isopropylidene-D-mannofuranose (18)

Methyl lithium (1.4 M in ether, 1.76 ml, 1.10 equiv) was added to a solution of 5-azido-6-O-tert-butyldimethylsilyl-5-deoxy-2,3-O-isopropylidene-D-mannono-1,4-lactone (17) (800 mg, 2.24 mmol) in tetrahydrofuran (15 ml) at −78° C. under nitrogen. The reaction mixture was stirred at −78° C. for 10 min when TLC (ethyl acetate:hexane, 1:3) showed no starting material (R$_f$ 0.21) and one major product (R$_f$ 0.27). The reaction mixture was quenched with saturated aqueous ammonium chloride solution (2 ml), diluted with ether (20 ml) and washed with water (2×20 ml); the organic layer was dried (magnesium sulphate) and the solvent removed to give, after purification by flash chromatography (ethyl acetate:hexane, 1:5), 1-C-methyl 5-azido-6-O-tert-butyldimethylsilyl-2,3-O-isopropylidene-D-mannofuranose (18), (602 mg, 72%), colorless oil, $\nu_{max}$ (CHCl$_3$): 3430 (br, OH), 2100 (N$_3$) cm$^{-1}$.

EXAMPLE 2

$\beta$-1-C-Methyl 6-O-tert-Butyldimethylsilyl-2,3-O-isopropylidene-deoxymannojirimycin (21)

1-C-Methyl 5-azido-6-O-tert-butyldimethylsilyl-2,3-O-isopropylidene-D-mannofuranose (18) (550 mg, 1.47 mmol) in ethyl acetate (15 ml) was stirred under an atmosphere of hydrogen in the presence of a catalyst of platinum(IV) oxide (100 mg) at room temperature for 40 h when TLC (ethyl acetate:hexane, 3:2) showed no starting material (R$_f$0.9) and one major product (R$_f$0.5). The catalyst was removed by filtration of the reaction mixture through celite and the solvent was removed to give, after purification by flash chromatography (ethyl acetate:hexane, 1:1), $\beta$-1-C-methyl 6-O-tert-butyldimethylsilyl-2,3-O-isopropylidene-deoxymannojirimycin (21), (420 mg, 86%), m.p. 93°–94° C., $[\alpha]_D^{20}$ −47.3° (c, 1.06 in CHCl$_3$), $\nu_{max}$(CHCl$_3$): 3470 (br, OH and NH) cm$^{-1}$ (Found: C, 58.23; H, 10.24; N, 4.08. C$_{16}$H$_{33}$NO$_4$Si requires: C, 58.01; H, 9.97; N, 4.23%).

EXAMPLE 3

$\beta$-L-Homofuconojirimycin, $\beta$-1-C-Methyl Deoxymannojirimycin, 2,6-Imino-2,6,7-trideoxy-L-glycero-D-mannohepitol (7)

$\beta$-1-C-Methyl 6-O-tert-butyldimethylsilyl-2,3-O-isopropylidene-deoxymannojirimycin (21) (175 mg, 0.53 mmol) in 50% aqueous trifluoroacetic acid (10 ml) was stirred at room temperature for 4 h and the reaction mixture was evaporated to dryness; the residue was washed with chloroform (2×5 ml) to give the trifluoroacetate salt of (7). Purification by ion exchange chromatography (Sigma CG-400 OH$^-$ form, then Aldrich 50x, 8-100, H+ form, eluted with 0.5 M aqueous ammonium hydroxide) gave the hygroscopic free base, $\beta$-L-homofuconojirimycin (7), (89 mg, 95%), m.p. 97°–98° C., $[\alpha]_D^{20}$ −21.5° (c, 1.07 in H$_2$O), $\nu_{max}$ (KBR): 3700–3000 (br, OH and NH) cm$^{-1}$. (Found: C, 47.16; H, 8.86; N, 7.67. C$_7$H$_{15}$NO$_4$ requires: C, 47.46; H, 8.47; N, 7.91%).

EXAMPLE 4

1-C-Vinyl 5-Azido-6-O-tert-butyldimethylsilyl-2,3-O-isopropylidene-D-mannofuranose (19)

Vinyl magnesium bromide (1.0 M in tetrahydrofuran, 1.0 ml, 1.05 equiv) was added to a solution of 5-azido-6-O-tert-butyldimethylsilyl-5-deoxy-2,3-O-isopropylidene-D-mannono-1,4-lactone (17) (340 mg, 0.95 mmol) in tetrahydrofuran (10 ml) at −78° C. under nitrogen. The reaction mixture was stirred at −78° C. for 10 min when TLC (ethyl acetate:hexane, 1:5) showed no starting material (R$_f$0.27) and one major product (R$_f$0.33). The reaction mixture was quenched with saturated aqueous ammonium chloride solution (2 ml), diluted with ether (20 ml) and washed with water (2×20 ml); the organic layer was dried (magnesium sulphate) and the solvent removed to give, after purification by flash chromatography (ethyl acetate:hexane, 1:7), 1-C-vinyl 5-azido-6-O-tert-butyldimethylsilyl-2,3-O-isopropylidene-D-mannofuranose (19), (331 mg, 90%), colorless oil, $\nu_{max}$(CHCl$_3$): 3410 (br, OH), 2100 (N$_3$), 1650 (weak, C=C) cm$^{-1}$.

EXAMPLE 5

$\beta$-1-C-Ethyl 6-O-tert-Butyldimethylsilyl-2,3-O-isopropylidene-deoxymannojirimycin (22)

The azidooctulose (19) (320 mg, 0.83 mmol) in ethyl acetate (10 ml) was stirred in an atmosphere of hydrogen in the presence of a catalyst of platinum(IV) oxide (50 mg) at room temperature for 18 h when TLC (ethyl acetate:hexane, 1:1) showed no starting material (R$_f$0.82 and one major product (R$_f$0.23). The catalyst was removed by filtration of the reaction mixture through celite and the solvent was removed to give, after purification by flash chromatography (ethyl acetate:hexane, 1:2), β-1-C-ethyl 6-O-tert-butyldimethylsilyl-2,3-O-isopropyl-idene-deoxymannojirimycin (22), (230 mg, 80%), m.p. 55°-56° C., $[\alpha]_D^{20} - 37.7°$ (c, 1.26 in CHCl$_3$), $v_{max}$ (CHCl$_3$) 3600-3100 (br, OH and NH) cm$^{-1}$. (Found: C, 59.25; H, 10.49; N, 3.79. C$_{17}$H$_{35}$NO$_4$Si requires: C, 59.13; H, 10.14; N, 4.06%).

EXAMPLE 6

β-1-C-Ethyl Deoxymannojirimycin (8)

The protected imino-octitol (22) (180 mg, 0.52 mmol) in 50% aqueous trifluoroacetic acid (14 ml) was stirred at room temperature for 4.5 h and the reaction mixture was evaporated to dryness; the residue was washed with chloroform (2×5 ml) to give the trifluoroacetate salt of (8). Purification by ion exchange chromatography (Sigma CG-400 OH$^-$ form, then Aldrich 50x, 8-100, H+ form, eluted with 0.5 M aqueous ammonium hydroxide) gave the very hygroscopic free base, β-1-C-ethyl deoxymannojirimycin (8), (95 mg, 95%), m.p. 54°-56° C., $[\alpha]_D^{20} -6.5°$ (c, 1.07 in H$_2$O), $v_{max}$ (KBr): 3700-3000 (br, OH and NH) cm$^{-1}$.

EXAMPLE 7

1-C-Phenyl 5-Azido-6-O-tert-butyldimethylsilyl-2,3-O-isopropylidene-D-mannofuranose (20)

Phenyl magnesium bromide (3.0 M in ether, 0.30 ml, 1.05 equiv) was added to a solution of 5-azido-6-O-tert-butyldimethylsilyl-5-deoxy-2,3-O-isopropylidene-D-mannono-1,4-lactone (17) (300 mg, 0.84 mmol) in tetrahydrofuran (10 ml) at −78° C. under nitrogen. The reaction mixture was stirred −78° C. for 10 min when TLC (ethyl acetate:hexane, 1:5) showed no starting material (R$_f$ 0.27) and one major product (R$_f$ 0.38). The reaction mixture was quenched with saturated aqueous ammonium chloride solution (2 ml), diluted with ether (20 ml) and washed with water (2×20 ml); the organic layer was dried (magnesium sulphate) and the solvent removed to give, after purification by flash chromatography (ethyl acetate:hexane, 1:7), 1-C-phenyl 5-azido-6-O-tert-butyldimethylsilyl-2,3-O-idene-D-mannofuranose (20), (314 mg, 86%), colorless oil, $v_{max}$ (CHCl$_3$): 3380 (br, OH), 2100 (N$_3$) cm$^{-1}$.

EXAMPLE 8

β-1-C-Phenyl 6-O-tert-Butyldimethylsilyl-2,3-O-isopropylidene-deoxymannojirimycin (23)

The ketose (20) (300 mg, 0.69 mmol) in ethyl acetate (10 ml) was stirred in an atmosphere of hydrogen in the presence of a catalyst of palladium black (50 mg) at room temperature for 35 h when TLC (ethyl acetate:-hexane, 1:1) showed no starting material (R$_f$ 0.85) and one product (R$_f$ 0.33). The catalyst was removed by filtration of the reaction mixture through celite and the solvent was removed to give, after purification by flash chromatography (ethyl acetate:hexane, 1:2), β-1-C-phenyl 6-O-tert-butyldimethylsilyl-2,3-O-isopropylidene-deoxymannojirimycin (23), (221 mg, 81%), m.p. 86°-87° C., $[\alpha]_D^{20}$ 0.0° (c, 1.05 in CHCl$_3$), $v_{max}$ (CHCl$_3$): 3600-3100 (br, OH and NH) cm$^{-1}$. (Found: C, 64.10; H, 9.26; N, 3.40, C$_{21}$H$_{35}$NO$_4$Si requires: C, 64.12; H, 8.91; N, 3.56%.

EXAMPLE 9

β-1-C-Phenyl Deoxymannojirimycin (9)

The protected phenyl deoxymannojirimycin (23) 0.46 mmol) in 50% aqueous trifluoroacetic acid (14 ml) was stirred at room temperature for 4 h and the reaction mixture was evaporated to dryness; the residue was washed with chloroform (2×5 ml) to give the trifluoroacetate salt of (9). Purification by ion exchange chromatography (Sigma CG-400 OH$^-$ form, then Aldrich 50x, 8-100, H+ form, eluted with 0.5 M aqueous ammonium hydroxide) gave the free base, β-1-C-phenyl deoxymannojirimycin (9), (99 mg, 90%), m.p. 77°-79° C., $[\alpha]_D^{20}$ +62.0° (c, 0.57 in H$_2$O), $v_{max}$ (KBr): 3600-3000 (br, OH and NH) cm$^{-1}$.

EXAMPLE 10

Inhibition of α-L-fucosidase by β-L-homofucanojirimycin (7) and 1-β-C-substituted deoxymannojirimycins (8) and (9) prepared above was demonstrated as follows:

MATERIALS AND METHODS

Tissue

Post-mortem human liver, which had been stored at −20° C. until required was homogenized in deionized water (50%, w/v) in a Potter-Elvehjem homogenizer and then centrifuged at 37,000 g for 30 min in an MSE 18 centrifuge. The resultant supernatant was used as the source of human glycosidases. A lyophilized extract of liver from Charonia lampas was obtained from Seikagaku Kogyo Co., Japan for the isolation of α-L-fucosidase by the published procedure of Iijima and Egami, J. Biochem. 70, 75-78 (1971).

Enzyme Assays

The glycosidase activities in an extract of human liver were assayed by using the appropriate fluorigenic 4-umbelliferyl glycoside substrate (Koch-Light, Haverhill, Suffolk, U.K.) with a concentration of 0.5 mM at the optimal pH for each enzyme [Burditt et al., Biochem. J. 189, 467-473 (1980)]. The specificity of the inhibitors was determined by assaying the glycosidases in the presence of and absence of a 1 mM solution of each compound. The nature of the inhibition of human α-L-fucosidase, the value of Ki determined by using the Dixon graphical procedure and the effect of pH on the inhibition were investigated as described previously by Al Daher et al., Biochem. J. 258, 613-615 (1989). Bovine epididymal and Charonia lampas α-L-fucosidase were assayed using para-nitrophenyl-α-L-fucopyranoside as substrate in phosphate-citrate buffer (McIlvaine), pH 6.0, and 0.005 M-sodium acetate buffer, pH 4.5 containing 0.15 M NaCl, respectively. The Lineweaver-Burk graphical procedure and secondary plots of the slope against inhibitor concentration were used to determine the nature of inhibition and the values of Ki for these activities.

The inhibitory results were as follows:

TABLE 1

Summary of inhibition of α-L-fucosidase and other glycosidases.

| Compound | pKa | Inhibition of α-L-fucosidase Ki (M) | Other specificities (% inhibition at 1 mM) |
|---|---|---|---|
| (4) DFJ | 8.4 | 1 × 10$^{-8}$ | |
| * MeFDJ | 7.8 | 5 × 10$^{-8}$ | N-acetyl-β-D-hexosaminidase (59%) |

TABLE 1-continued

Summary of inhibition of α-L-fucosidase and other glycosidases.

| Compound | pKa | Inhibition of α-L-fucosidase Ki (M) | Other specificities (% inhibition at 1 mM) |
|---|---|---|---|
| (10) DMJ | 7.2 | $5 \times 10^{-6}$ | α-D-mannosidase (64%) |
| (7) β-HFJ | 7.1 | $1 \times 10^{-8}$ | β-D-galactosidase (27%) |
| (8) β-EtDMJ | 7.8 | $7 \times 10^{-8}$ | N-acetyl-β-D-hexosaminidase (36%) |
| (9) β-PheDMJ | 6.3 | $1 \times 10^{-6}$ | N-acetyl-β-D-hexosaminidase (50%) |

* Synthesized from DFJ as described by Fleet et al., FEBS Lett 237, 128–132 (1988).

TABLE 2

Comparative inhibition of α-L-fucosidase by compounds 7, 8 & 9

| Compound | Ki (M) Bovine epididymis | Ki (M) C. lampas |
|---|---|---|
| (7) | $2 \times 10^{-8}$ | $1.4 \times 10^{-7}$ |
| (8) | $2 \times 10^{-6}$ | $5.8 \times 10^{-7}$ |
| (9) | $5.5 \times 10^{-6}$ | $2 \times 10^{-3}$ |

Various other examples will be apparent to the person skilled in the art after reading the present disclosure without departing from the spirit and scope of the invention. It is intended that all such other examples be included within the scope of the appended claims.

What is claimed:

1. A fucosidase inhibitor selected from the group consisting of 1-β-C-substituted deoxymannojirimycins in which the 1-β-C substituent is an alkyl group having from one to six carbon atoms or phenyl.

2. β-1-C-methyl deoxymannojirimycin.

3. β-1-C-ethyl deoxymannojirimycin.

4. β-1-C-phenyl deoxymannojirimycin.

5. A method of inhibiting α-L-fucosidase in a biological fluid comprising subjecting said biological fluid containing Δ-L-fucosidase to an inhibitory effective amount of a compound of claim 1.

6. A method for the production of a β-1-C-substituted deoxymannojirimycin of claim 1 comprising reacting 5-azido-6-O-tert-butyldimethylsilyl-5-deoxy-2,3-O-isopropylidene-D-mannono-1,4-lactone with an alkylating reagent selected from the group consisting of methyl lithium, vinyl magnesium bromide and phenyl magnesium bromide to give a 1-C-adduct of said 5-azido-6-O-tert-butyldimethylsilyl-5-deoxy-2,3-O-isopropylidene-D-mannono-1,4-lactone followed by catalytic hydrogenation of said adduct to give a corresponding hydroxyl-protected β-1-C-substituted deoxymannojirimycin and then hydrolytic removal of the silyl and isopropylidene protecting groups from said hydroxyl-protected β-1-C-substituted deoxymannojirimycin.

* * * * *